United States Patent
Parris et al.

[11] Patent Number: 5,976,115
[45] Date of Patent: Nov. 2, 1999

[54] BLUNT CANNULA SPIKE ADAPTER ASSEMBLY

[75] Inventors: Wayne M. Parris, Anaheim; William A. Sperko, Yorba Linda; Peter N. Cassimatis, San Clemente; Martin V. Shabaz, Santa Ana, all of Calif.

[73] Assignee: B. Braun Medical, Inc., Irvine, Calif.

[21] Appl. No.: 08/947,929

[22] Filed: Oct. 9, 1997

[51] Int. Cl.⁶ .................................................. A61M 25/00
[52] U.S. Cl. ........................ 604/283; 604/411; 604/415; 604/905
[58] Field of Search .................................. 604/186, 187, 604/188, 192, 195, 197, 198, 162, 163, 165, 240, 242, 263, 411, 412, 415, 905

[56] References Cited

U.S. PATENT DOCUMENTS

| | | | |
|---|---|---|---|
| D. 313,277 | 12/1990 | Haining | D24/53 |
| 2,102,704 | 12/1937 | Hein | 128/218 |
| 2,559,474 | 7/1951 | Son | 128/215 |
| 2,564,804 | 8/1951 | Everett | 128/221 |
| 2,746,455 | 5/1956 | Abel | 128/221 |
| 2,770,236 | 11/1956 | Utley et al. | 128/221 |
| 2,817,372 | 12/1957 | Barr, Sr. et al. | 141/288 |
| 2,911,972 | 11/1959 | Elinger | 128/216 |
| 2,929,510 | 3/1960 | Penn | 211/60 |
| 2,954,768 | 10/1960 | Hamilton | 128/221 |
| 2,989,053 | 6/1961 | Hamilton | 128/221 |
| 3,030,953 | 4/1962 | Koehn | 128/214 |
| 3,526,340 | 9/1970 | Heinz | 222/80 |
| 3,645,268 | 2/1972 | Capote | 128/347 |
| 3,826,260 | 7/1974 | Killinger | 128/272 |
| 3,831,814 | 8/1974 | Bulter | 222/81 |
| 3,995,630 | 12/1976 | van de Veerdonk | 128/218 DA |
| 4,096,860 | 6/1978 | McLaughlin | 128/214.4 |
| 4,123,091 | 10/1978 | Cosentino et al. | 285/39 |
| 4,153,057 | 5/1979 | Köbel | 128/272.1 |
| 4,244,364 | 1/1981 | Grushkin | 128/214 |

(List continued on next page.)

FOREIGN PATENT DOCUMENTS

| | | |
|---|---|---|
| 0127781 | 12/1884 | European Pat. Off. . |
| 0395758 | 11/1990 | European Pat. Off. . |
| 1171578 | 1/1959 | France . |
| 486715 | 9/1937 | United Kingdom . |
| 843744 | 8/1960 | United Kingdom . |
| 927020 | 5/1963 | United Kingdom . |

OTHER PUBLICATIONS

William R. Seebaugh et al., *An Automated Device for Aseptically Aspirating Serum From Blood Collection Tubes,* vol. BME–33, No. 6, Jun. 1986, pp. 609–616.

*Primary Examiner*—Corrine McDermott
*Assistant Examiner*—David J. Cho
*Attorney, Agent, or Firm*—Christie, Parker & Hale, LLP

[57] ABSTRACT

A spike adapter and blunt cannula spike adapter assembly comprises a spike adapter having a hollow chamber extending axially therethrough from a first body end to a second body end. The hollow chamber is adapted to receive and accommodate attachment with a blunt cannula therein. A spike shaft projects axially outwardly away from the adapter body second end and has a sharpened tip at a distal end. A spike cover is disposed over the spike shaft to cover the sharpened tip. The spike shaft includes a hollow channel extending axially therethrough that is adapted to accommodate placement of a blunt cannula shaft concentrically therein to allow the blunt cannula to access medicine containers having unslit septums or stoppers. The spike adapter body includes axially extending grooves that accommodate blunt cannula tongues therein to form a tongue and groove attachment therebetween. Notches project from surface portions of the adapter body disposed across the grooves, and are designed to engage blunt cannula tongues to lock the blunt cannula into the spike adapter. The adapter body includes surface portions that are diametrically opposed to the grooves and that are deformable in a radially inwardly direction to permit the elastic deformation of the adapter body to unlock the tongues from the respective notches.

28 Claims, 6 Drawing Sheets

U.S. PATENT DOCUMENTS

| | | | |
|---|---|---|---|
| 4,328,802 | 5/1982 | Curley et al. | 128/272.1 |
| 4,369,781 | 1/1983 | Gilson et al. | 128/214 |
| 4,377,165 | 3/1983 | Luther et al. | 128/214.4 |
| 4,410,321 | 10/1983 | Pearson et al. | 604/56 |
| 4,449,973 | 5/1984 | Luther | 604/161 |
| 4,542,749 | 9/1985 | Caselgrandi et al. | 128/752 |
| 4,559,043 | 12/1985 | Whitehouse et al. | 604/201 |
| 4,569,675 | 2/1986 | Prosl et al. | 604/175 |
| 4,573,967 | 3/1986 | Hargrove et al. | 604/56 |
| 4,573,981 | 3/1986 | McFarlane | 604/263 |
| 4,573,993 | 3/1986 | Hoag et al. | 604/411 |
| 4,589,879 | 5/1986 | Pearson | 604/411 |
| 4,610,671 | 9/1986 | Luther | 604/168 |
| 4,624,667 | 11/1986 | Rutnarak | 604/414 |
| 4,632,671 | 12/1986 | Dalton | 604/174 |
| 4,638,809 | 1/1987 | Kuperus | 128/653 |
| 4,650,475 | 3/1987 | Smith et al. | 604/189 |
| 4,668,221 | 5/1987 | Luther | 604/164 |
| 4,702,735 | 10/1987 | Luther et al. | 604/161 |
| 4,747,836 | 5/1988 | Luther | 604/198 |
| 4,762,516 | 8/1988 | Luther et al. | 604/164 |
| 4,790,817 | 12/1988 | Luther | 604/53 |
| 4,804,366 | 2/1989 | Zdeb et al. | 604/85 |
| 4,826,500 | 5/1989 | Rautsola | 604/411 |
| 4,832,696 | 5/1989 | Luther et al. | 604/164 |
| 4,834,152 | 5/1989 | Howson et al. | 141/286 |
| 4,838,871 | 6/1989 | Luther | 604/192 |
| 4,842,591 | 6/1989 | Luther | 604/283 |
| 4,861,341 | 8/1989 | Woodburn | 604/175 |
| 4,869,717 | 9/1989 | Adair | 604/51 |
| 4,892,518 | 1/1990 | Cupp et al. | 604/93 |
| 4,909,791 | 3/1990 | Norelli | 604/192 |
| 4,935,020 | 6/1990 | Brodén | 604/411 |
| 4,950,252 | 8/1990 | Luther et al. | 604/198 |
| 4,964,854 | 10/1990 | Luther | 604/166 |
| 4,969,883 | 11/1990 | Gilbert et al. | 604/414 |
| 4,994,027 | 2/1991 | Rohrbough | 604/88 |
| 5,053,014 | 10/1991 | Van Heugten | 604/167 |
| 5,098,394 | 3/1992 | Luther | 604/167 |
| 5,112,315 | 5/1992 | Gloyer et al. | 604/195 |
| 5,122,120 | 6/1992 | Wallace | 604/164 |
| 5,135,513 | 8/1992 | Meyer et al. | 604/240 |
| 5,167,642 | 12/1992 | Fowles | 604/263 |
| 5,211,638 | 5/1993 | Dudar et al. | 604/283 |
| 5,312,345 | 5/1994 | Cole | 604/110 |
| 5,368,607 | 11/1994 | Freitas | 606/172 |
| 5,411,499 | 5/1995 | Dudar et al. | 604/411 |
| 5,454,409 | 10/1995 | McAffer et al. | 141/329 |
| 5,470,327 | 11/1995 | Helgren et al. | 604/411 |
| 5,547,471 | 8/1996 | Thompson et al. | 604/87 |
| 5,584,819 | 12/1996 | Kopfer | 604/239 |

BLUNT CANNULA SPIKE ADAPTER ASSEMBLY

FIELD OF THE INVENTION

This invention relates to a spike assembly for accessing a drug vial and the like and, more particularly, to a spike adapter assembly that is constructed to accommodate attachment and fluid-flow communication with a blunt cannula member to enable its use for piercing and penetrating an unslit closure.

BACKGROUND OF THE INVENTION

The use of a blunt cannula for penetrating access devices having a preslit septum, without tearing or displacing the septum is known. The use of such blunt cannula is not designed for and is not capable of penetrating solid unslit rubber stoppers or septums of drug vials or other medicine containers. Pointed cannulas, needles, and drug vial spikes are well known instruments that can be used to pierce and penetrate such solid unslit rubber stoppers or septums of drug vials or other medicine containers.

In the practice of combining and dispensing medicine it is sometimes necessary to access different containers that comprise both solid and preslit septums. For example, it may be necessary to access a first drug container containing a liquid medicine to remove a quantity of the medicine via a syringe and the like, and then inject the quantity of medicine into a fluid path accessed by an injection site or the like having a preslit septum. The practice of accessing a preslit septum using a sharp-tipped device, such as a sharpened cannula, needle or drug spike, can cause the septum to be physically damaged in the form of coring or laceration, which can result in subsequent leakage.

The use of sharp-tipped instruments is also not desired for uses other than those specifically requiring use of the same, e.g., to access a solid septum, due to the potential hazards associated with infectious agents. Personnel using such sharped-tipped instruments are trained to do so with great care. However, instances are known to occur where a person using such a sharp-tipped instrument punctures themself while attempting to perform an operation that does not require the use of such sharp-tipped instrument, e.g., when accessing a preslit septum. It may be that such past accidents, and future accidents, could be avoided by selecting the proper instrument for the particular operation. The choice of selecting the proper instrument for a particular operation may not always be an attractive or an available option, given the time window within which the operation must be performed, or given the ready availability of instruments. For example, an emergency situation may call for the rapid mixing and/or dispensing of medicine, or the unavailability of instruments may call for improvisation.

Figure 1:
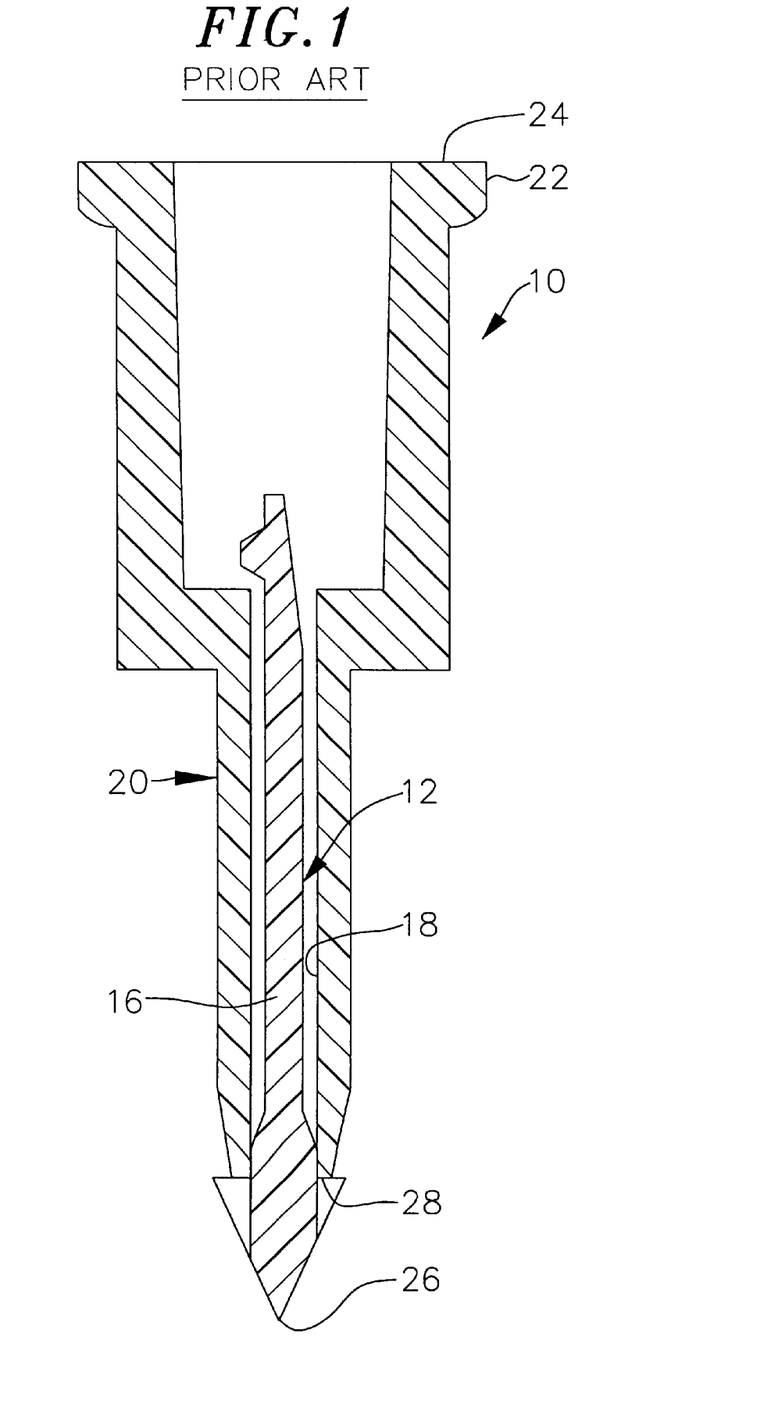
FIG. 1 is a cross-sectional side view of a conventional device for adapting a blunt cannula for accessing a solid septum.

In an effort to overcome the difficulties and potential hazards relating to the use of the proper instrument for accessing both preslit and unslit septums, devices have been constructed for insertion within a fluid-flow passage of a blunt cannula for providing such cannula with a pointed tip. Referring to FIG. 1, U.S. Pat. No. 5,411,499 discloses such a device 10 generally comprising a piercing member 12 having a shaft 16 that is disposed within a fluid-flow channel 18 of a blunt cannula 20. The blunt cannula 20 has a Luer flange 22 at a first end 24, for connecting to an engaging structure (not shown). The piercing member 12 comprises a pointed tip 26 at a distal end of the shaft 16 that projects from a tip 28 of the cannula fluid-flow channel 18 having a tapered outside surface, to permit the blunt cannula to be used to access a solid septum. However, the construction of the device does not permit accessing more than one container that comprises a solid septum, as the piercing member 12 is designed to be removed from the cannula 20, and be retained within the solid septum, when the cannula is withdrawn from the solid septum.

It is, therefore, desired that a device be constructed that facilitates the use of a blunt cannula for accessing both solid and preslit septums. It is desired that the device be constructed so that it will enable the blunt cannula to be used for accessing more than one container comprising a solid septum without the need to replace assembly components or use additional assemblies. To promote application flexibility, it is also desired that such device be constructed to facilitate use with existing blunt cannula designs. It is further desired that the device be constructed in a manner that promotes ease of use without additional equipment, tools or training.

SUMMARY OF THE INVENTION

A spike adapter and blunt cannula spike adapter assembly, constructed according to principles of this invention, comprises a spike adapter having a hollow chamber extending axially therethrough from a first body end to a second body end. The hollow chamber is adapted to receive and accommodate attachment with a blunt cannula therein. A spike shaft projects axially outwardly away from the spike adapter body second end and has a sharpened tip at a distal end. A spike cover is disposed over the spike shaft to cover the sharpened tip. The spike shaft includes a hollow channel extending axially therethrough that is adapted to accommodate placement of a blunt cannula shaft concentrically therein, thereby allowing use of the blunt cannula to access medicine containers having unslit septums or stoppers.

The spike adapter body includes axially extending grooves disposed therein that receive and accommodate tongues projecting radially away from a blunt cannula body, forming a tongue and groove attachment therebetween. The spike adapter body includes notches, projecting from surface portions of the spike adapter body that extend across the grooves. The notches are sized and positioned to engage an adjacent portion of respective blunt cannula tongues to releasably lock the blunt cannula into the spike adapter upon sufficient axial displacement of the blunt cannula within the spike adapter body. The spike adapter body includes surface portions that are diametrically opposed to the grooves and that are deformable in a radially inwardly direction to cause the spike adapter body to be elastically deformed a sufficient amount to release the tongues from the respective notches, thereby facilitating release of the blunt cannula from the spike adapter.

The blunt cannula spike adapter assembly of this invention permits use of a blunt cannula for accessing medicine containers having an unslit or solid septum or stopper, and enables such use for accessing more than one such medicine container without having to replace assembly components or use additional assemblies. To promote application flexibility, the spike adapter is constructed to facilitate use with existing blunt cannulas designs.

DESCRIPTION OF THE DRAWINGS

These and other features and advantages of the present invention will become appreciated as the same becomes better understood with reference to the specification, claims and drawings wherein:

DETAILED DESCRIPTION OF THE INVENTION

A blunt cannula spike adapter assembly, constructed according to principles of this invention, comprises a blunt cannula spike adapter that is designed to accept and releasably attach with a blunt cannula to enable use of the blunt cannula to access containers that have a solid or unslit stopper or septum. The blunt cannula spike adapter is designed to enable repeated use of the blunt cannula to access more than one container having a solid or unslit stopper or septum without having to replace the spike adapter or without having to replace assembly components or use additional assemblies.

Figures 2, 3:
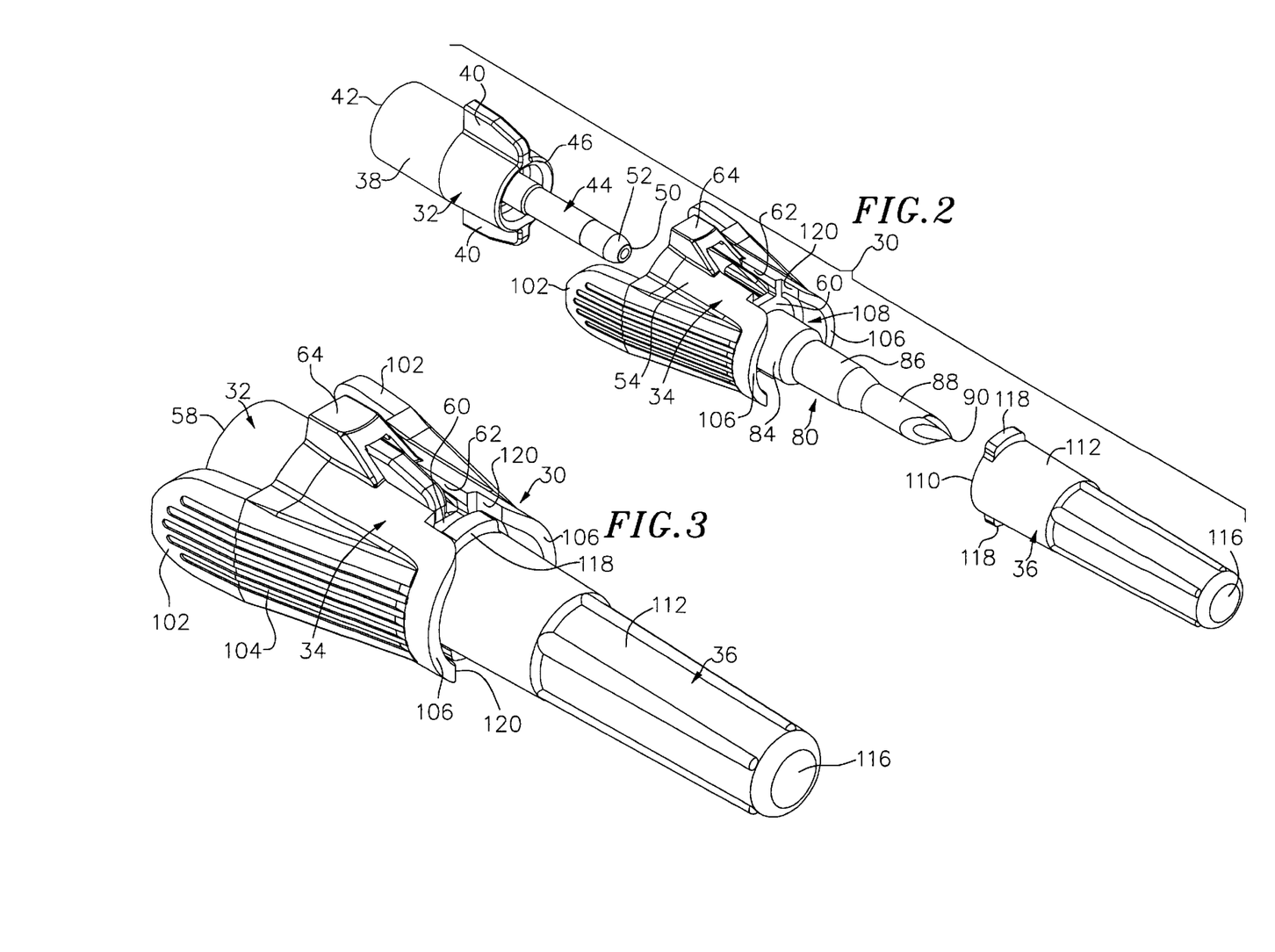
FIG. 2 is an exploded perspective side view of a blunt cannula spike adapter assembly constructed according to principles of this invention.
FIG. 3 is a perspective side view of an assembled blunt cannula spike adapter assembly constructed according to principles of this invention.
Figure 4:
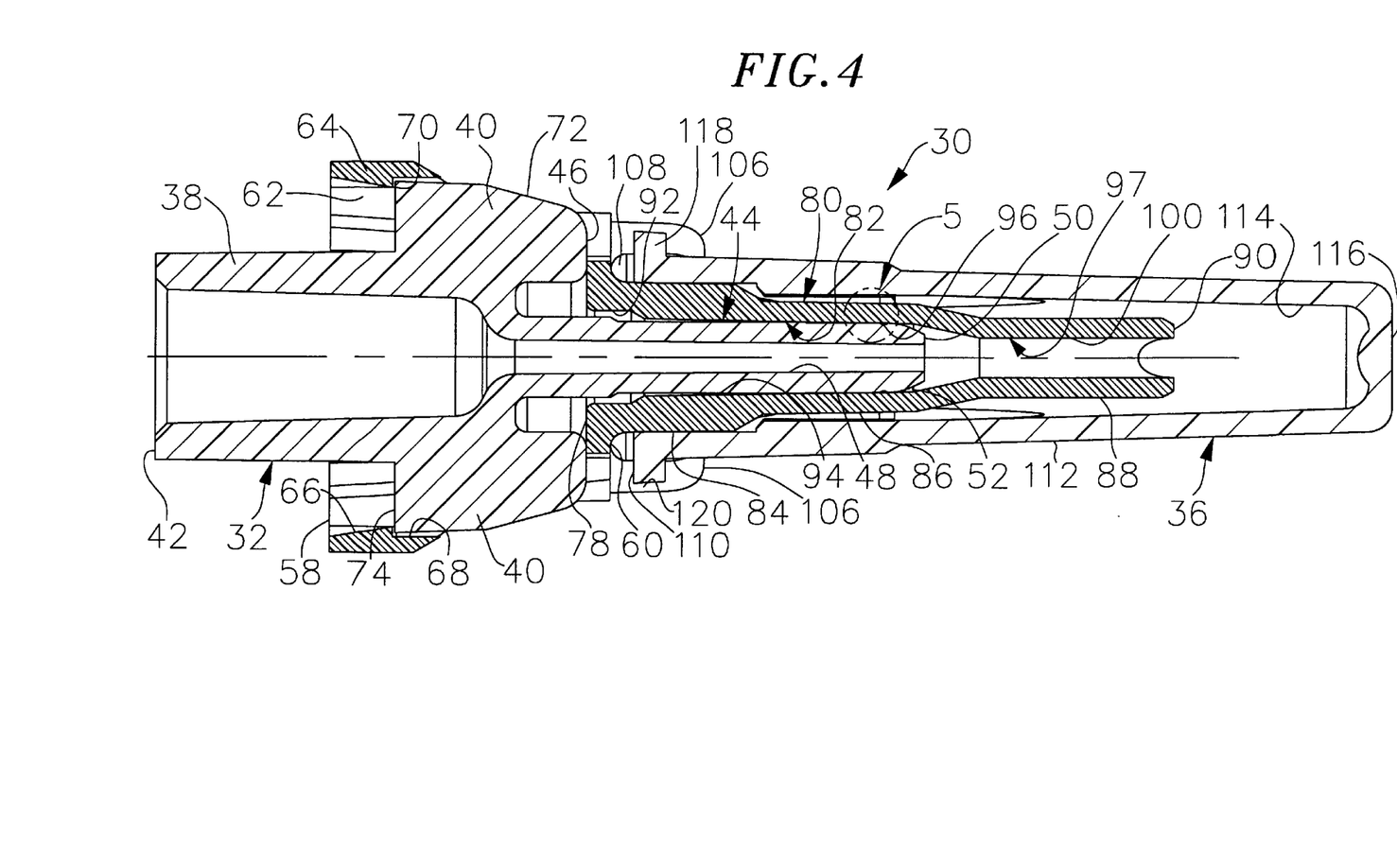
FIG. 4 is a cross-sectional side view of the assembled blunt cannula spike adapter assembly of FIG. 3.

FIG. 2 illustrates the primary components of a blunt cannula spike adapter assembly 30, constructed according to principles of this invention, in an unassembled state. Moving from left to right across FIG. 2, the assembly 30 comprises a blunt cannula 32 that is releasably attached to a blunt cannula spike adapter 34, and a spike sheath 36 disposed over a tip of a spike projecting from the spike adapter 34. FIG. 3 illustrates the blunt cannula spike adapter assembly 30 of FIG. 2 in an assembled state. FIG. 4 is a cross-sectional side view of the blunt cannula spike adapter assembly in an assembled state, illustrating the interaction among the primary assembly components.

Referring to FIGS. 2 and 4, moving from left to right across the figures, the blunt cannula 32 comprises a generally cylindrical body 38 having a pair of diametrically opposed tongues 40 projecting radially outwardly therefrom. The cannula body 38 has a first end 42 that is adapted for connecting with a fluid dispensing device such as a syringe or the like, and has a shaft 44 at an opposite second end 46 of the body 38 that extends axially a distance therefrom and that defines a hollow fluid-flow channel 48 therein (as shown in FIG. 4). The cannula body shaft 44 includes a blunt tip 50 that has a radiused outside surface 52. Constructed in this manner, the blunt cannula shaft 44 is adapted to penetrate preslit septums or stoppers of medicine containers, injection sites and the like without coring or otherwise damaging the same, but cannot be used to pierce or penetrate medicine containers having solid or unslit stoppers or septums.

Figure 6:
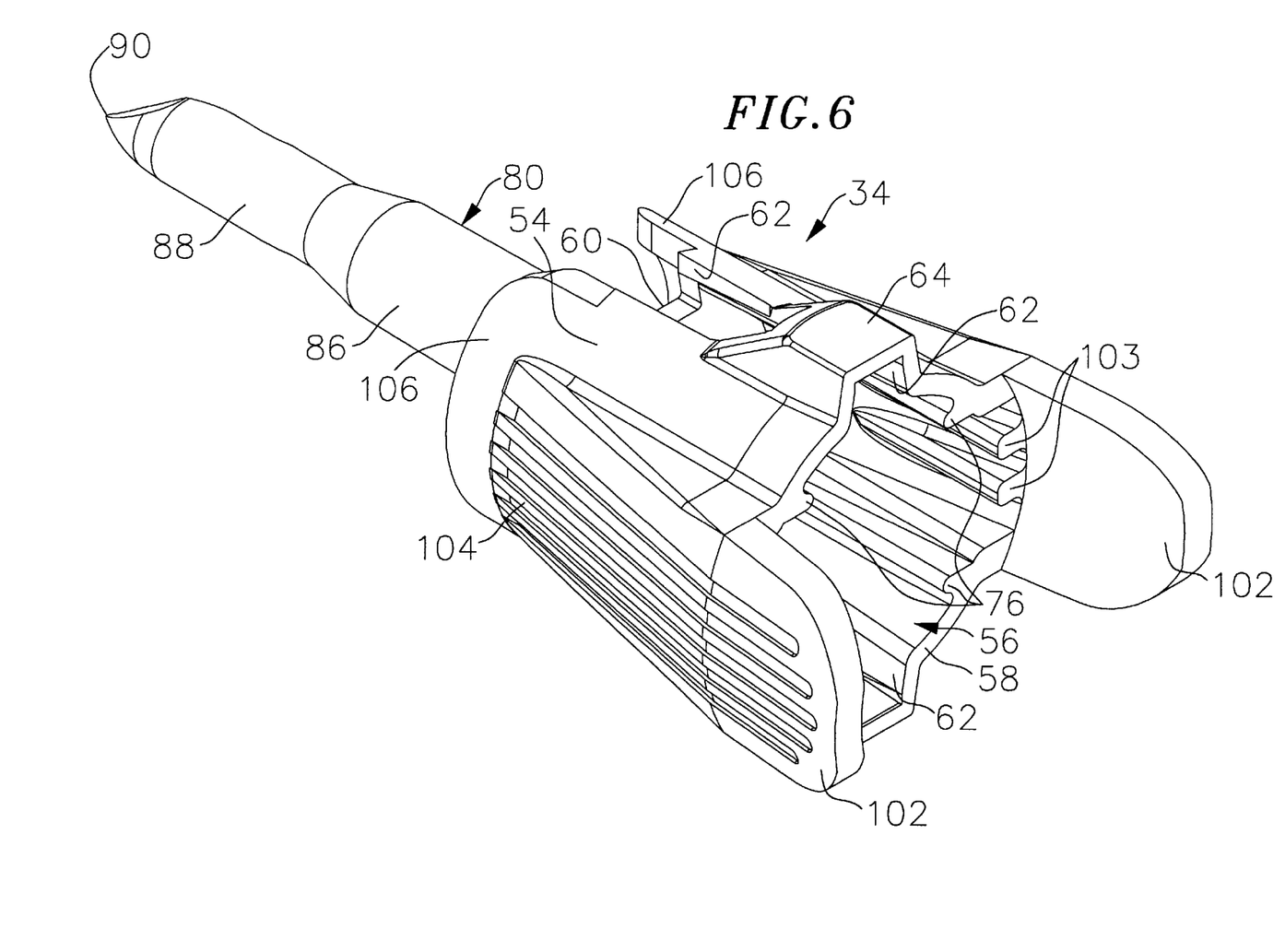
FIG. 6 is a rear elevation of a blunt cannula spike adapter of the blunt cannula spike adapter assembly of FIGS. 2 and 3.

As best illustrated in FIG. 6, the blunt cannula spike adapter 34 comprises a spike adapter body 54 defining a hollow chamber 56 therein that extends axially from a first spike adapter body end 58, located at a rear-facing end of the spike adapter, to an opposite second spike adapter body end 60, located at a forward-facing end of the spike adapter. The hollow chamber 56 is constructed to accommodate placement of at least a portion of the blunt cannula body 38 therein. The spike adapter body 54 includes means for receiving and forming a releasable locking attachment with the blunt cannula body 38 and, more specifically, for forming a locking attachment with the tongues 40 extending from the cannula body. In an example embodiment, the spike adapter 34 comprises a pair of diametrically opposed grooves 62 that each extend axially along the spike adapter body 54, and that are formed from axially cut-out portions of the spike adapter body. The grooves 62 are sized and positioned to accommodate placement of respective tongues 40 therein to form a tongue and groove attachment. The use of the grooves, to provide a tongue and groove attachment with the blunt cannula tongues, also prevents the blunt cannula 32 from rotating within the spike adapter 34, thereby facilitating installation of the blunt cannula spike adapter assembly onto a syringe or the like.

It is to be understood that although an example attachment mechanism and structure for providing an attachment between the blunt cannula 32 and spike adapter 34 has been described and illustrated, other well known attachment mechanisms and structures can be used. For example, attachment between the blunt cannula and spike adapter can be provided by friction attachment means or other types of mechanical releasably locking structures that are capable of providing a snap fit. An example alternative releasably locking structure can be one provided by a spike adapter body 54 that has a body portion designed to snap over a complementary body portion of the blunt cannula when the blunt cannula is displaced axially within a desired axial distance within the spike adapter body.

The grooves 62 extend axially from the spike adapter body first end 58 to the spike adapter body second end 60 and essentially split the spike adapter body axially into two symmetrically opposed halves. The spike adapter body comprises a pair of diametrically opposed bridges 64 that each project radially outwardly a distance from the spike adapter body, and that are disposed over respective grooves 62. The bridges 64 serve to both retain the two spike adapter body halves together and comprise means for engaging and retaining the cannula body tongues 40 therein. As best illustrated in FIG. 4, moving axially away from the spike adapter body first end 58, each bridge 64 has an inside surface that includes a tapered section 66 that extends axially a distance to a non-tapered section 68. A radially inwardly projecting notch 70 is formed at the transition between the tapered and non-tapered inside surface sections. Each bridge inside surface tapered section 66 is designed to accommodate placement of a respective tongue leading edge 72 therein as the blunt cannula 32 is inserted into the spike adapter chamber 56.

Each notch 70 is positioned and is configured to abut against a respective tongue rear-facing edge 74, when the blunt cannula 32 is disposed axially a desired distance within the spike adapter body chamber 56, to releasably lock the blunt cannula therein and to prevent it from being unintentionally withdrawn from the spike adapter. As will be discussed in greater detail below, the use of the grooves to form two spike adapter body half sections and the use of the bridges disposed over the grooves, provide a spike adapter body that is elastically deformable when compressed radially, such elastic deformation be desired and serving as the mechanism for effecting release of the tongues 40 from respective bridge notches 70.

A releasable locking attachment is formed between the blunt cannula 32 and the spike adapter 34 by placing the blunt cannula shaft 44 into the spike adapter body hollow chamber 56 so that the blunt cannula tongues 40 are positioned within respective grooves 62. The blunt cannula is displaced axially within the spike adapter chamber until the blunt cannula tongues 40 pass into respective spike adapter body bridges 64, and the tongue rear-facing edges 74 passes over respective notches 70, thereby preventing outwardly directed axial displacement of the blunt cannula.

Referring to FIG. 6, the spike adapter body chamber 56 comprises a number of rails 76 that project radially inwardly a distance into the chamber to make contact with an outside surface of the blunt cannula body 38 when the spike adapter body is elastically deformed, by deflecting diametrically opposed portions of the spike adapter body radially inwardly, to effect release of the attachment with the blunt cannula. The rails are designed to center the blunt cannula body 38 radially within the spike adapter chamber 56 so that it is aligned and coaxial within the spike adapter body. Centering the blunt cannula body to effect release of the locking attachment is desired to enable simultaneous release of both tongues 40 from respective notches 70. Without the use of such rails to center the cannula body, the inward deflection of the spike adapter body can cause the cannula body to be displaced radially therein, causing the preferential release of one tongue and notch without the other. This can result in either the non-simultaneous release of both tongues, or can in fact prevent a tongue and notch from becoming disengaged, thereby preventing the blunt cannula from being removed from the spike adapter.

In an example embodiment, the spike adapter chamber 56 comprises four rails 76 that are positioned radially along the chamber inside surface at 90 degree angles with respect to one another, and that are positioned at 45 degree angles with respect to the spike adapter body grooves 62. The rails project a desired distance into the chamber 56, extend axially therein from the first spike adapter body end 58 to the second spike adapter body end 60, and are designed to make contact with the outside surface of the blunt cannula and center the blunt cannula radially within the body chamber upon elastic deformation of the spike adapter body as described above.

Referring back to FIGS. 2 to 4, the spike adapter body chamber 56 comprises a radially inwardly directed shoulder 78 disposed at the spike adapter body second end 60. The shoulder 78 is positioned axially within the spike adapter body chamber 56 to accommodate placement of the blunt cannula body second end 46 thereagainst when the blunt cannula is disposed completely within the spike adapter body chamber 56. Moving axially away from the spike adapter body second end 60, the spike adapter 34 comprises a spike shaft 80 having a hollow spike channel 82 extending internally therethrough. The spike shaft 80 has an outside surface comprising three different diameter sections. A spike shaft first diameter section 84 extends axially a distance from the spike adapter body second end 60 and has a diameter that is sized to facilitate placement of the spike sheath 36 thereover to form a releasable interference fit therewith. A spike shaft second diameter section 86 extends axially a distance from the shaft first diameter section 84, and is sized smaller than the shaft first diameter section. A spike shaft third diameter section 88 extends axially from the shaft second diameter section 86 to a sharpened tip 90 of the spike shaft 80. The shaft third diameter section 88 is sized smaller than the shaft second diameter section 86.

The spike shaft 80 is designed having a stepped or multi-diameter outside surface to make the spike adapter easier to use when accessing a medicine container. Specifically, the spike shaft is designed having a relatively smaller diameter shaft third diameter section 88 adjacent the sharpened tip 90, with a step increase in diameter moving to the shaft second diameter section 86 a sufficient distance away from the tip 90, to improve the ability of the spike shaft to penetrate an unslit septum or stopper. This feature makes the spike adapter both easier and safer to use.

The spike channel 82 comprises a first diameter section 92 extending a distance axially away from the spike adapter body second end 60, and that extends axially along a distance of the spike shaft 80 outside surface first diameter section 84. The channel first diameter section 92 is sized larger than an outside diameter of the blunt cannula shaft 44 to accommodate its placement concentrically therein. A channel second diameter section 94 extends axially a distance from the channel first diameter section 92, is smaller than the channel first diameter section 92, and extends axially along a distance of the spike outside surface first and second diameters sections 84 and 86. The channel second diameter section 94 is sized slightly larger than the outside diameter of the blunt cannula shaft 44 to accommodate its placement concentrically therein and also to provide a close-tolerance fit.

Figure 5:
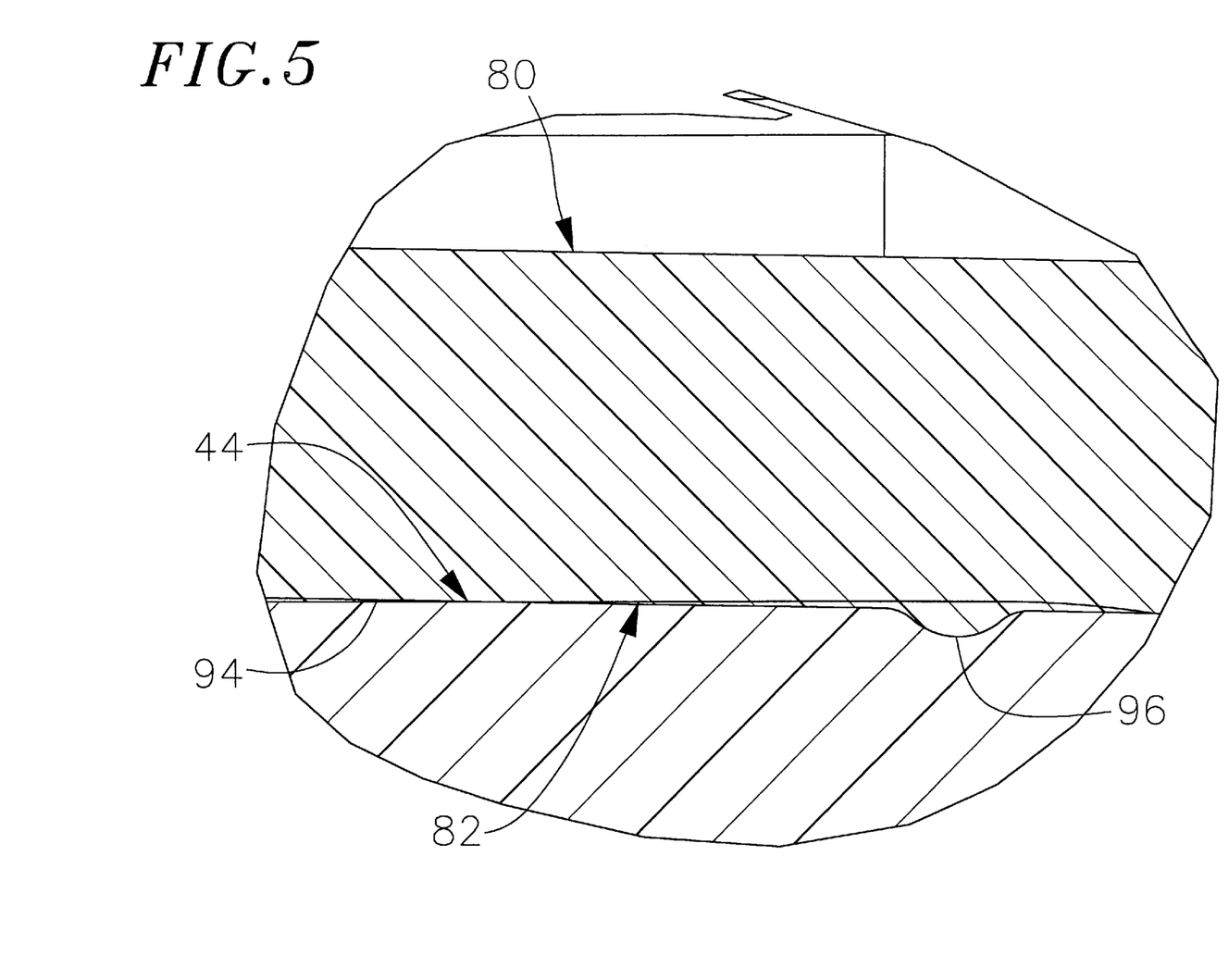
FIG. 5 is an exploded sectional view of section 5 of FIG. 4.

Referring to FIGS. 4 and 5, the channel second diameter section 94 includes means for forming a leak-tight fitting against the blunt cannula shaft 44 therein. In an example embodiment, the chamber second diameter section 94 includes a circumferential ridge 96 that projects radially inwardly into the spike channel 82. The ridge 96 is positioned near an axial end of the channel second diameter section 94 to cooperate with an outside surface section of the blunt cannula shaft 44 near its tip 50 to provide a releasable interference fit therewith. The interference fit between the blunt cannula shaft 44 and the channel second diameter section 94 provides an air and liquid-tight seal therebetween to contain the passage of fluid to only a fluid-flow portion 97 of the spike channel 82 that extends axially from the ridge 96 to the spike tip 90.

Additionally, the presence of such interference fit forms an air-tight seal between the blunt cannula shaft 44 and the spike channel 82 to prevent air from being drawn, from between the channel 82 and shaft 44 surfaces, when using the blunt cannula spike adapter assembly to withdraw medication from a medicine container. Alternatively, rather than designing a ridge that projects from a surface of the spike channel 82, the blunt cannula shaft 44 can be constructed having a circumferentially extending ridge (not shown) that projects outwardly a distance therefrom to form a leak-tight seal against an adjacent spike shaft channel surface.

A channel third diameter section 100 extends axially from the channel second diameter section 94 to the spike tip 90. The channel third diameter section 100 is smaller than the channel second diameter section 94 and extends axially along the spike outside surface third diameter section 88. It is desired that the channel third diameter section 100 be sized somewhat similar to the fluid-flow channel 48 running through the blunt cannula shaft 44 to minimize any fluid transport effects when passing fluid therebetween. Additionally, a transition between the second and third chamber diameter sections is positioned within the spike channel 82 next to the blunt cannula shaft tip 50 when the blunt cannula is releasably attached to the spike adapter.

Referring to FIGS. 2, 3 and 6, the spike adapter 34 includes means for releasing the blunt cannula 32 from its locked axial placement within the spike adapter body hollow chamber 56. In an example embodiment, the means is in the form of a pair of wings 102 that each extend radially outwardly from diametrically opposed positions of the spike adapter body 54. The wings 102 are integral with the body to form a one-piece construction, and are positioned 90 degrees with respect to the spike adapter body grooves 62 and bridges 64, i.e., each wings extends from each spike adapter body half section. In an example embodiment, the wings 102 project away from the spike adapter body at an angel of approximately 30 degrees with reference to an axis running axially through the spike adapter hollow chamber 56, and extend a distance of approximately 0.25 inches from the spike adapter body first end 58.

Each wing extends axially a distance away from the spike adapter body first end 58 to both facilitate easy grasping between one's fingers, and act as a lever to impose a sufficient force onto the spike adapter body to cause the body to elastically deform in a manner that simultaneously reduces the distance between the wings 102 and increases the distance between the spike adapter body bridges 64. Using the wings 102 to elastically deform the spike adapter body in this manner, causes the notches 70 along the inside surface of the bridges to be moved radially away from respective cannula tongues 40. As discussed above, the presence of the rails 76 within the spike adapter body chamber 56 centers the cannula body therein so that the bridges 64 deflect in an equidistant amount away from respective cannula body tongues 40, thereby facilitating simultaneous release of each tongue. Additionally, the wings 102 act as a protector to prevent touch contamination of the blunt cannula shaft 44 upon removal of the blunt cannula 32 from the spike adapter 34.

The wings 102 each include a number of ridges 104 that extend axially along an outside surface of the wings from each wing end to the spike adapter body 54. The ridges 104 provide structural rigidity to the wings 102 so that when pressed inwardly each, rather than bending without causing the spike adapter body to elastically deform, such inwardly directed force is transmitted to the spike adapter body to effect a desired degree of elastic deformation. In an example embodiment, each wing comprises four ridges. However, it is understood that the number of ridges disposed on the wings can vary depending on such factors as the wing length, wing thickness, ridge length, ridge thickness and the like. The ridges 104 also facilitate grasping the wings between one's fingers, e.g., to prevent slipping.

Referring to FIG. 6, the spike adapter chamber 56 includes a number of ribs 103 disposed along an inside surface of the wings 102, that project radially inwardly a distance into the chamber 56, and that extend axially a distance from the spike adapter body first end 58. The ribs 103 are designed to prevent the blunt cannula 32 from being inserted incorrectly into the spike adapter chamber by preventing placement of the blunt cannula tongues 40 therepast. In an example embodiment, the spike adapter chamber 56 includes a pair of ribs 103 that project from the inside surface of each wing 102. The ribs 103 are sized and spaced to interfere with and prevent placement of the blunt cannula tongues 40 therepast in the event that the blunt cannula is incorrectly positioned, i.e., out of position by approximately 90 degrees, vis-a-vis the spike adapter chamber 56.

Although an example means for releasing the blunt cannula has been disclosed and illustrated, it is to be understood that other types of mechanical structures can be employed for releasing the blunt cannula, depending on the type of attachment mechanism that is used. For example, rather than using discrete wings, the spike adapter 34 can be configured having a continuous skirt (not shown) that projects axially a distance from the spike adapter body first end 58, which skirt can be movable radially inwardly to cause a desired elastic deformation of the spike adapter body 54.

The spike adapter body 54 includes a pair of collars 106 that each extend axially outwardly a distance away from the spike adapter body second end 60. The collars 106 are diametrically opposed from one another, are separated by the spike adapter body grooves 62, and are positioned axially in line with the wings 102. An annular space 108 (as best illustrated in FIG. 2) is disposed immediately adjacent the spike adapter body second end 60 and is defined along an outside diameter by the collars 106, and along an inside diameter by the adapter spike 80. The annular space 108 is designed to accommodate a first end 110 of the spike sheath 36 therein when the sheath is installed over the spike 80. The collars 106 extend axially away from the spike adapter body a sufficient distance to provide an annular space 108 having a desired depth to accommodate the sheath first end 1 10 and provide a desired interference fit therewith.

The spike sheath 36 comprises a body 112 having a hollow chamber 114 (illustrated in FIG. 4) disposed therein that extends between the open first end 110 and a closed second end 116. The spike sheath hollow chamber 114 has an inside diameter at the first end 110 that is sized to form a tight releasable interference fit with the spike shaft 80 outside surface first diameter section 84 so that, when placed over the spike shaft, the sheath will resist loosening or accidental removal. The spike sheath body 112 may also comprise a pair of tabs 116 that project radially outwardly a distance therefrom. The tabs 118 are diametrically opposed from one another and are positioned at the sheath first end 110 to cooperate with slots 120, disposed within the spike adapter body 54 at the spike adapter body second end 60, that are axially in line with the grooves 62. The slots 120 are formed between the pair of collars 106. The sheath tabs 118 are sized to fit within respective slots 120 to further prevent the sheath from being accidentally loosened or removed from the spike shaft 80.

Figure 7:
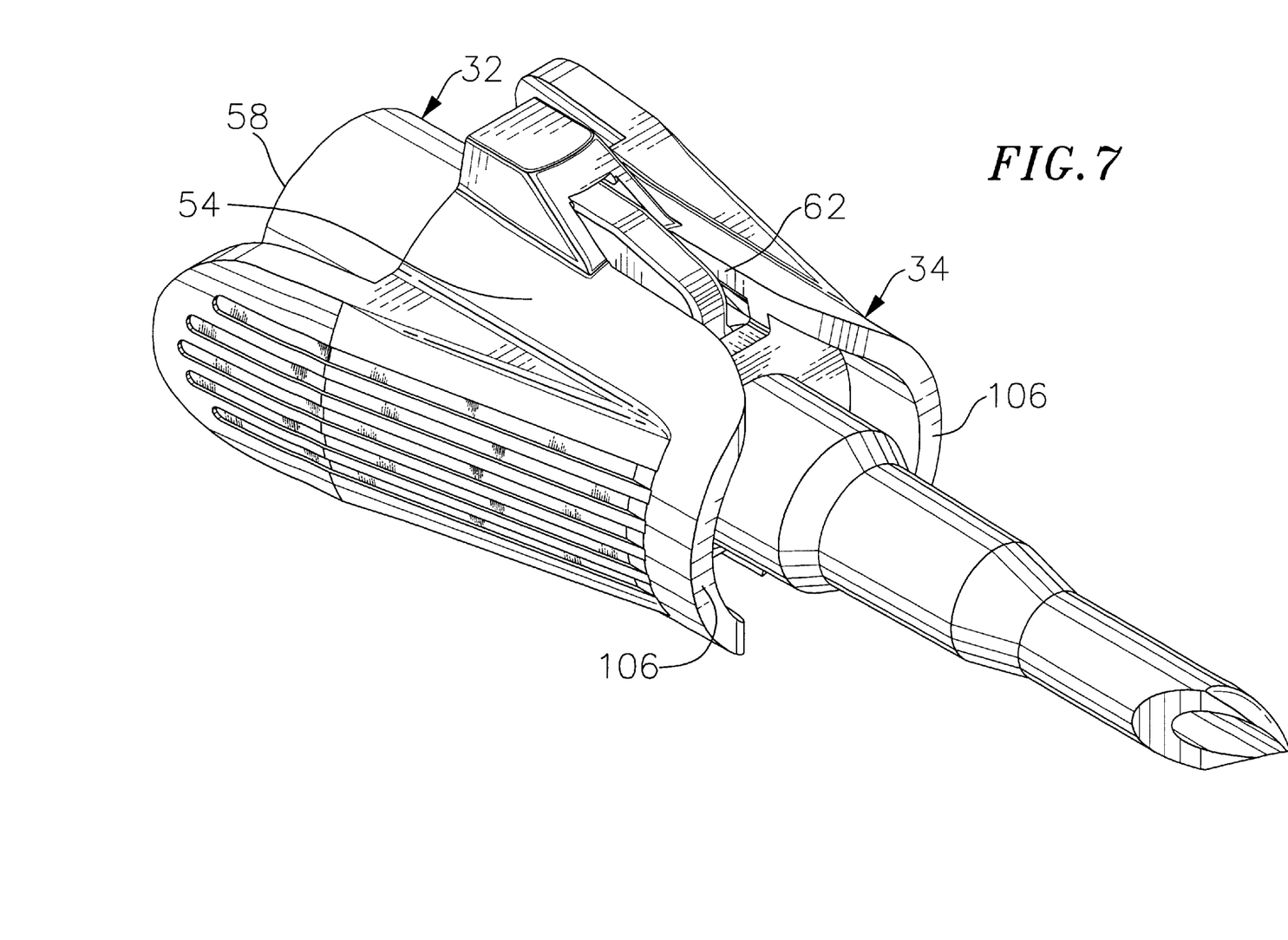
FIG. 7 is a front elevation of an alternative blunt cannula adapter of this invention.

Referring to FIG. 7, the spike adapter body 54 can be configured having collars 106 that taper towards the grooves 62 as they each move axially towards the spike adapter body first end 58. In such embodiment, the sheath tabs 118 are disposed between the tapered walls of respective collars 106, rather than being disposed within a slot. However, in either embodiment the walls of the collars 106 provide a close fit with respective sheath tabs 118 to prevent accidental loosening or removal when installed over the spike shaft 80.

Referring to FIGS. 2, 3 and 4 the blunt cannula spike adapter assembly 30 is formed by inserting the blunt cannula shaft 44, and at least a portion of the blunt cannula body 38, into the spike adapter hollow chamber 56 and axially displacing the blunt cannula a sufficient distance therein to forming a releasable locking attachment therebetween. When the blunt cannula is releasably attached to the spike adapter the blunt cannula fluid-flow channel 48 is in fluid-flow communication with the fluid-flow portion 97 of the spike channel 82, and a leak-tight fitting is formed therebetween. The spike sheath 36 is disposed over the spike shaft 80 to cover the same until the spike adapter is to be used to pierce and penetrate a container comprising a solid or unslit stopper or septum.

The three components of the blunt cannula spike adapter assembly can be made according to techniques of manufacturing, and from materials of construction, conventionally used in the medical device industry. For example, the blunt cannula 32, spike adapter 34, and spike sheath 36 can be made by mold process from the group of polymeric materials including polyester resins such as a copolyester resin manufactured by Eastman Chemical Co., under the product name EASTALLOY, polypropylene or high density polyethylene resins manufactured by Eastman Chemical Co., under the product name TENITE, acrylonitrile styrenes such as a acrylonitrile butadiene styrene (ABS) manufactured by BASF under the product name TERLUX, acrylic resins such as an acrylic resin manufactured by Novacor under the product name ZYLER, and polycarbonate resins such as a modified polycarbonate with green concentrate manufactured by General Electric under the product name LEXAN. A preferred material for the blunt cannula is polycarbonate manufactured by General Electric under the product name LEXAN 1110. A preferred material for the spike adapter is ABS manufactured by BASF under the product name TERLUX 2802. A preferred material for the spike sheath is polyethylene manufactured by Eastman Chemical Co., under the product name TENITE 830A.

Blunt cannula spike adapter assemblies, constructed according to principles of this invention, are preassembled and packaged in a blister pack or equivalent. The outside diameter of the spike shaft 80 is siliconized to aid insertion into a drug vial or the like to facilitate ease of insertion. The blunt cannula shaft 44 is also siliconized to aid insertion once separate from the spike adapter into a preslit septum.

The blunt cannula spike adapter assembly permits the use of a blunt cannula to access a container comprising a solid or unslit stopper or septum by attaching the blunt cannula 32 to a desired fluid dispensing instrument, e.g., a syringe, removing the spike sheath 36 from the spike adapter 34, and using the sharpened tip 90 of the spike shaft 80 to permit the combined blunt cannula 32 and spike adapter 34 to pierce and penetrate the stopper or septum. A feature of the spike adapter assembly is that it is a one-piece construction, forming a two piece assembly when combined with the blunt cannula to permit use of the blunt cannula to access unslit or solid septums or stoppers. Another feature of the combined blunt cannula and spike adapter is that it can be used to access more than one container comprising a solid or unslit stopper or septum without having to provide replacement parts. For example, the combined blunt cannula and spike adapter can be used to access a first container comprising a liquid medicine by piercing and penetrating the solid stopper or septum of the container with the sharpened tip of the spike shaft. With the spike shaft tip disposed within the liquid medicine, a volume of the medicine can be withdrawn from the container, via the connected respective fluid-flow channel 48 and fluid-flow portion 97 of the spike channel 82 of the combined blunt cannula and spike adapter, via a syringe that is connected to the blunt cannula. The combined blunt cannula and spike adapter can be withdrawn from the first container and used to access a second container in the same manner comprising a powdered medicine and having a solid stopper or septum. Once inserted within the second container, the volume of liquid medicine within the syringe can be dispensed into the second container, through the connected respective fluid-flow channel 48 and fluid-flow portion 97 of the spike channel 82 of the combined blunt cannula and spike adapter, for mixing with the powdered medicine in the second container to form a desired medicine mixture. The medicine mixture can be withdrawn from the second container via the combined blunt cannula and spike adapter by the syringe, and the combined blunt cannula spike adapter removed from the second container.

To facilitate dispensement of the medicine mixture into a container comprising a preslit septum, such as a preslit injection site and the like, and to prevent the possibility of personal injury or damage to the septum, the combined syringe and blunt cannula is removed from the spike adapter and the blunt cannula is inserted into the preslit septum for subsequent dispensement of the medicine mixture. Constructed in this manner, the blunt cannula spike adapter assembly enables use of the blunt cannula to access both solid and preslit stoppers or septums, thereby increasing the flexibility of the blunt cannula as an instrument for liquid dispensement and reducing the possible danger of injury associated with not using the proper instrument for a particular application, e.g., not using a sharp-tipped spike, cannula or needle for accessing containers having a preslit septum.

Although limited embodiments of the blunt cannula spike adapter assembly and its components have been specifically described and illustrated herein, many modifications and variations will be apparent to those skilled in the art. Accordingly, it is to be understood that, within the scope of the appended claims, the blunt cannula spike adapter assembly and its components constructed according to principles of this invention may be embodied other than as specifically described herein.

We claim:

1. A spike adapter and blunt cannula assembly comprising:
   a spike adapter including:
      a body having a hollow chamber extending axially therethrough from a first body end to a second body end;
      a spike shaft projecting axially outwardly away from the body second end, the spike shaft having a sharpened tip at a distal end and having a hollow channel extending axially therethrough;
   a blunt cannula releasably attached to the spike adapter the blunt cannula having a cannula body and a hollow shaft extending outwardly therefrom, the cannula shaft being disposed within the spike adapter body hollow chamber and spike adapter shaft hollow channel;
   means for providing a releasably locking attachment with the blunt cannula disposed at the spike adapter body first body end.

2. The spike adapter as recited in claim 1 wherein the means for providing comprises complementary tongues and grooves along opposed adjacent sections of the spike adapter body and blunt cannula body, one of the spike adapter body or blunt cannula body further comprising notches that abut against adjacent surface of the tongues after the blunt cannula is displaced axially a desired distance within the hollow chamber to provide a locking attachment therewith.

3. The spike adapter as recited in claim 2 wherein the spike adapter body comprises an outer surface portion that is moved radially inwardly to cause a portion of the spike adapter body to deform elastically and cause the notches to move away from respective tongues to release the locking attachment.

4. The spike adapter as recited in claim 3 wherein the spike adapter body comprises a pair of diametrically opposed wings that are adapted to be moved radially inwardly to cause a portion of the spike adapter body to deform elastically, wherein the wings each extend axially a distance along an outside surface of the spike adapter body and project axially a distance from the spike adapter body first end, wherein the grooves are disposed between the wings.

5. The spike adapter as recited in claim 1 further comprising means for radially aligning a blunt cannula within the spike adapter body chamber.

6. The spike adapter as recited in claim 5 wherein the means for radially aligning comprises a number of rails disposed within the hollow chamber and extending axially therein, the rails projecting inwardly into the chamber a sufficient distance to contact outer surface portions of the blunt cannula.

7. The spike adapter as recited in claim 1 wherein the spike adapter shaft has a first diameter section that extends axially a distance away from the sharpened shaft tip, and a second shaft diameter section that extends axially a distance along the shaft from the first diameter section towards the spike adapter second body end, the first diameter section being smaller in diameter than the second diameter section.

8. The spike adapter as recited in claim 1 further comprising means disposed within the hollow channel for forming a leak-tight seal with the blunt cannula shaft.

9. The spike adapter as recited in claim 8 wherein the means for forming a leak-tight seal comprises a circumferential ridge that projects radially inwardly into the hollow channel a sufficient distance to contact an adjacent outer surface of the blunt cannula shaft to form a leak-tight seal therebetween.

10. A spike adapter for use with a blunt cannula comprising:
  a body having a hollow chamber extending axially therethrough from a first body end to a second body end;
  a spike shaft projecting axially outwardly away from the body second end, the spike shaft having a sharpened tip at a distal end and having a hollow channel extending axially therethrough that is adapted to accommodate placement of a blunt cannula shaft concentrically therein, the spike shaft includes a first diameter section extending axially away from the sharpened tip that is smaller in diameter than a second diameter section that extends axially away from the first diameter section towards the second body end;
  a pair of diametrically opposed grooves extending axially along the body from the body first end for forming a tongue and groove attachment with tongues of a blunt cannula;
  notches disposed within outwardly projecting portions of the spike adapter body that are disposed over each groove, wherein the notches are adapted to engage and retain the tongues of a blunt cannula disposed within the grooves;
  wings extending axially along an outside surface of the spike adapter body for elastically deforming the spike adapter body radially inwardly to move the notches away from tongues of a blunt cannula, wherein the wings are diametrically opposed from one another and are positioned at 90 degree intervals from the grooves.

11. The spike adapter as recited in claim 10 wherein the spike hollow channel comprises a circumferentially extending ridge that projects radially inwardly into the hollow channel a sufficient distance to contact and form a leak-tight seal with an outside surface of a blunt cannula shaft that is disposed concentrically therein.

12. The spike adapter as recited in claim 10 wherein the hollow chamber comprises a number of rails disposed axially therein that project inwardly into the chamber a sufficient distance to contact outer surface portions of the blunt cannula and radially center the blunt cannula therein when the spike adapter body is deformed elastically.

13. The spike adapter as recited in claim 10 wherein the wings comprise a number of ridges extending axially along an outside surface to the spike adapter body to reinforce the wings.

14. A blunt cannula spike adapter assembly comprising the spike adapter as recited in claim 10 and further comprising a blunt cannula including:

a cannula body having a fluid-flow channel extending therethrough from a cannula body first end to the cannula body second end;
  a cannula shaft extending axially away from the cannula body second end, wherein the cannula shaft is disposed concentrically within the spike hollow channel; and
  tongues extending radially away from the cannula body, wherein the tongues are diametrically opposed from one another and are disposed within respective spike adapter body grooves, wherein the notches are engaged against a rear-facing edge of the tongues to prevent outward axial displacement of the blunt cannula from the spike adapter.

15. A blunt cannula spike adapter assembly comprising:
  a spike adapter comprising:
    a body having a hollow chamber extending axially therethrough from a first body end to a second body end;
    a spike shaft projecting axially outwardly away from the body second end, the spike shaft having a sharpened tip at a distal end and having a hollow channel extending axially therethrough; and
    grooves extending axially along the body;
  a blunt cannula disposed at least partially within the hollow chamber and comprising:
    a cannula body having a cannula shaft extending radially therefrom, the cannula shaft being disposed concentrically within the spike hollow channel and in fluid-flow communication therewith; and
    tongues projecting radially outwardly from the cannula body and disposed within respective spike adapter body grooves to form a tongue and groove attachment therebetween;
  wherein the spike adapter body comprises means for retaining the tongues within respective the grooves to prevent outwardly axial displacement of the blunt cannula from spike adapter hollow chamber; and
  wherein the spike adapter body comprises means for releasing the means for retaining.

16. The assembly as recited in claim 15 wherein the spike adapter body comprises a pair of grooves that are diametrically opposed from one another and that each extend axially between the spike adapter body first and second ends, and wherein the blunt cannula body comprises a pair of tongues that are diametrically opposed from on another for placement within the grooves.

17. The assembly as recited in claim 16 wherein the means for retaining comprises notches that project outwardly from spike adapter body portions that extend over and across the grooves, wherein the notches are positioned to connect with a rear-facing edge of respective tongues when the blunt cannula body is axially displaced a desired distance into the hollow chamber to prevent outwardly axial displacement of the blunt cannula from spike adapter hollow chamber.

18. The assembly as recited in claim 17 wherein the means for releasing comprises an outer surface portion of the spike adapter body that is adapted to be deflected radially inwardly to cause the spike adapter body to be elastically deformed, and wherein the outer surface portions are positioned so that its radial deflection causes the notches to be moved radially outwardly and away from engagement with respective tongues.

19. The assembly as recited in claim 18 wherein the outer surface portions of the spike adapter body comprise wings that extend axially along the spike adapter body and that project axially a distance from the spike adapter body first end, and wherein the wings are positioned diametrically opposed from one another and at 90 degree intervals from the grooves.

20. The assembly as recited in claim 18 wherein the hollow chamber comprises a number of rails disposed axially therein that project inwardly into the chamber a sufficient distance to contact outer surface portions of the blunt cannula when the spike adapter body is deformed elastically to radially center the blunt cannula therein.

21. The assembly as recited in claim 19 wherein the wings comprise a number of ridges extending axially along an outside surface to the spike adapter body to reinforce the wings.

22. The assembly as recited in claim 15 wherein the spike hollow channel further comprises a circumferentially extending ridge that projects radially outwardly therefrom, and that contacts an outside surface of the blunt cannula shaft to form a leak-tight seal therebetween.

23. The assembly as recited in claim 15 wherein the spike shaft comprises:
   a first diameter section that extends axially a distance away from the sharpened tip; and
   a second diameter section that extends a distance axially away from the first diameter section towards the spike adapter body second end, and that is greater in diameter than the first diameter section.

24. The assembly as recited in claim 15 further comprising a cover releasably attached over the spike shaft.

25. A blunt cannula spike adapter assembly comprising:
   a spike adapter comprising:
      a body having a hollow chamber extending axially therethrough from a first body end to a second body end;
      a spike shaft projecting axially outwardly away from the body second end, the spike shaft having a sharpened tip at a distal end and having a hollow channel extending axially therethrough, wherein the spike shaft has a first diameter section extending axially away from the sharpened tip that is smaller in diameter than a second diameter section that extends axially away from the first diameter section towards the spike adapter body first body end; and
      a pair of diametrically opposed grooves extending axially along the body;
   a blunt cannula disposed at least partially within the hollow chamber and comprising:
      a cannula body having a cannula shaft extending radially therefrom, the cannula shaft being disposed concentrically within the spike hollow channel and in fluid-flow communication therewith, and wherein the spike hollow channel includes a circumferentially extending ridge that projects axially a sufficient distance into the channel to contact and form a leak-tight seal against an outside surface of the cannula shaft; and
      a pair of diametrically opposed tongues projecting radially outwardly from the cannula body and disposed within respective spike adapter body grooves to form a tongue and groove attachment therebetween.

26. The assembly as recited in claim 25 wherein the spike adapter body further comprises notches projecting from a pair of spike adapter body portions that are each disposed over a respective groove, and wherein the notches engage an adjacent surface of respective tongues to form a releasably locking attachment therewith when the blunt cannula is displaced axially within the spike adapter body hollow chamber a desired amount.

27. The assembly as recited in claim 26 wherein the spike adapter body further comprises outside surface portions that are positioned diametrically opposed from the grooves and are movable in a radially inwardly direction to cause the spike adapter body to be elastically deformed an amount sufficient to disengage the notches from the tongues.

28. The assembly as recited in claim 27 wherein the outside surface portions are wings that extend axially along the spike adapter body and that project a distance away from the spike adapter body first end, where in the wings project angularly outwardly away from the spike adapter body.

* * * * *

UNITED STATES PATENT AND TRADEMARK OFFICE
CERTIFICATE OF CORRECTION

PATENT NO. : 5,976,115  
DATED : November 2, 1999  
INVENTOR(S) : Wayne M. Parris; William A. Sperko; Peter N. Cassimatis; Martin V. Shabaz It is certified that error appears in the above-identified patent and that said Letters Patent is hereby corrected as shown below:

Column 10,  
Line 44, change "surface" to -- surfaces --.

Column 12,  
Line 36, after "respective" delete "the".  
Line 46, replace "on another" with -- one another --.

Column 14,  
Line 39, change "where in" to -- wherein --.

Signed and Sealed this

Thirtieth Day of October, 2001

Attest:

NICHOLAS P. GODICI  
Acting Director of the United States Patent and Trademark Office Attesting Officer